(12) United States Patent
Langlois

(10) Patent No.: US 10,062,145 B2
(45) Date of Patent: Aug. 28, 2018

(54) METHOD FOR MAPPING CRYSTAL ORIENTATIONS IN A SAMPLE MADE OF A POLYCRYSTALLINE MATERIAL

(71) Applicants: INSTITUT NATIONAL DES SCIENCES APPLIQUEES DE LYON, Villeurbanne (FR); CENTRE NATIONAL DE LA RECHERCHE SCIENTIFIQUE (CNRS), Paris (FR); UNIVERSITE CLAUDE BERNARD LYON 1, Villeurbanne (FR)

(72) Inventor: Cyril Langlois, Lyons (FR)

(73) Assignees: INSTITUT NATIONAL DES SCIENCES APPLIQUEES DE LYON, Villeurbanne (FR); CENTRE NATIONAL DE LA RECHERCHE SCIENTIFIQUE (CNRS), Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 105 days.

(21) Appl. No.: 15/113,417

(22) PCT Filed: Jan. 23, 2015

(86) PCT No.: PCT/EP2015/051313
§ 371 (c)(1),
(2) Date: Jul. 21, 2016

(87) PCT Pub. No.: WO2015/113898
PCT Pub. Date: Aug. 6, 2015

(65) Prior Publication Data
US 2017/0011518 A1    Jan. 12, 2017

(30) Foreign Application Priority Data

Jan. 28, 2014 (FR) ...................... 14 00207

(51) Int. Cl.
*G06K 9/00* (2006.01)
*G06T 3/00* (2006.01)
(Continued)

(52) U.S. Cl.
CPC ....... *G06T 3/0056* (2013.01); *G01N 23/2251* (2013.01); *G01N 23/2255* (2013.01);
(Continued)

(58) Field of Classification Search
None
See application file for complete search history.

(56) References Cited

FOREIGN PATENT DOCUMENTS

FR    2988841    10/2013

OTHER PUBLICATIONS

Vasilisa Veligura et al: "Channeling in helium ion microscopy: Mapping of crystal orientation", Beilstein Journal of Nanotechnology, vol. 3, Jul. 10, 2012, pp. 501-506.*
(Continued)

*Primary Examiner* — Idowu O Osifade
(74) *Attorney, Agent, or Firm* — Womble Bond Dickinson (US) LLP

(57) ABSTRACT

The invention relates to a method for mapping the crystal orientations of a polycrystalline material, the method comprising:
receiving (21) a series of images of the polycrystalline material, which images are acquired by an acquiring device in respective irradiation geometries;
estimating (22) at least one intensity profile for at least one point of the material from the series of images, each intensity profile representing the intensity associated with the point in question as a function of irradiation geometry; and
determining (24) a crystal orientation for each point in question of the material by comparing (23) the intensity
(Continued)

profile associated with said point in question to theoretical signatures of intensity profiles of known crystal orientations, which signatures are contained in a database.

23 Claims, 4 Drawing Sheets

(51) Int. Cl.
    *G01N 23/2251*     (2018.01)
    *G01N 23/2255*     (2018.01)
    *G06T 7/00*     (2017.01)
    *G06T 7/70*     (2017.01)
    *G06T 7/73*     (2017.01)
    *G06T 7/174*     (2017.01)

(52) U.S. Cl.
    CPC ............... *G06T 7/174* (2017.01); *G06T 7/70* (2017.01); *G06T 7/73* (2017.01); *G06T 7/97* (2017.01); *G01N 2223/3307* (2013.01); *G01N 2223/405* (2013.01); *G01N 2223/606* (2013.01); *G06T 2207/10061* (2013.01); *G06T 2207/10152* (2013.01)

(56) References Cited

OTHER PUBLICATIONS

Uchic M D et al: "3D microstructural characterization of nickel superalloys via serialsectioning using a dual beam FIB-SEM", Scripta Materialia, vol. 55, Jul. 1, 2006, pp. 23-28.*
International Search Report dated Mar. 16, 2015, International Application No. PCT/EP2015/051313.
French Search Report with English Translation Cover Sheet dated Jul. 7, 2014, French Application No. 1400207.
Kameda, Jun , et al., "Morphological analyses of minute crystals by using stereo-photogrammetric scanning electron microscopy and electron back-scattered diffraction", *Journal of Microscopy*, vol. 228, No. 3, (Dec. 1, 2007), 358-365.
Suzuki, Seiichi , "Features of Transmission EBSD and its Application", *JOM*. vol. 65, No. 9, (Jul. 27, 2013), 1254-1263.
Uchic, Michael D., et al., "3D microstructural characterization of nickel superalloys via serial-sectioning using a dual beam FIB-SEM", *Scripta Materialia, Elsevier*, Amsterdam, NL, vol. 55, No. 1, (Jul. 1, 2006), 23-28.
Veligura, Vailisa , et al., "Channeling in helium ion microscopy: Mapping of crystal orientation", *Beilstein Journal of Nanotechnology*, vol. 3, (Jul. 10, 2012), 501-506.

\* cited by examiner

METHOD FOR MAPPING CRYSTAL ORIENTATIONS IN A SAMPLE MADE OF A POLYCRYSTALLINE MATERIAL

TECHNICAL FIELD

The present invention relates to the general technical field of the characterization of a sample made of a polycrystalline material. These materials are for example ceramics, metals, etc.

Polycrystalline materials are solid materials made up of a plurality of small crystals—called "grains"—of various crystal orientations and sizes, as opposed to single-crystal materials which consist of one and only one crystal and amorphous materials that do not have long-range order.

Most materials (in the fields of microelectronics, future energy sources, alloys, ceramics and minerals) are composed of crystals of different sizes, shapes and structures.

The anisotropy of polycrystalline materials affects their characteristics and especially their mechanical properties (crack resistance, yield strength, etc.) or even their electrical properties in multiple ways.

It is therefore very important to be able to determine the crystal orientation of the grains of a polycrystalline material.

DESCRIPTION OF THE PRIOR ART

Currently, a technique known as electron backscatter diffraction (EBSD) is used to characterize crystals.

EBSD is a micro structural crystallographic technique especially allowing the crystal orientation of many single-crystal or polycrystalline materials to be measured. EBSD may be used to index and identify crystalline phases belonging to the seven crystal systems, namely:
  the triclinic crystal system,
  the monoclinic crystal system,
  the orthorhombic crystal system,
  the tetragonal crystal system,
  the trigonal crystal system,
  the hexagonal crystal system, and
  the cubic crystal system.

EBSD is carried out with a scanning electron microscope (SEM) equipped with an EBSD detector including at least one phosphorescent screen, a compact objective and a low-light CCD video camera.

To perform an EBSD measurement, a polycrystalline sample is placed in a chamber of the SEM, with a large angle (~70° to the horizontal) to the diffraction video camera, in order to increase the contrast of the backscattered electron micrograph.

The phosphorescent screen is located inside the specimen chamber of the SEM at an angle of about 90° to the axis of the beam and is coupled to a compact objective that focuses the image produced on the phosphorescent screen toward the CCD video camera.

In this configuration, some of the electrons that reach the sample are backscattered and, before escaping the sample, are diffracted by the crystal planes of the sample when the Bragg condition, which is dependent on the spacing of the periodic planes of the atomic lattice of the structure, is met. Some of these diffracted electrons strike and excite the phosphorescent screen, causing it to fluoresce.

An electron backscatter diffraction pattern (or EBSP) is formed when a plurality of different planes diffract electrons to form Kikuchi lines (or Kikuchi bands), which correspond to each of the diffracting planes of the lattice.

If the system geometry is well described, it is possible to relate the bands present in the EBSP pattern to the crystal phase and orientation of the material located in the electron interaction volume.

To do this, the acquired image is processed using an algorithm allowing the orientation of each grain to be characterized.

One drawback of the aforementioned technique is that it requires the assembly composed of the phosphorescent screen and the objective of the CCD video camera to be installed inside the chamber of the SEM, thereby increasing the cost of the latter.

Another drawback relates to the image acquisition time which may be very long (i.e. several hours) depending on the desired image quality. Specifically, the higher the required spatial resolution of the image, the longer the image acquisition time must be.

Another drawback of this technique is that the electron beam emitted toward the sample must make an angle of about 70° to the normal to the surface of the sample if Kikuchi lines are to be obtained. Such an inclination of the electron beam with respect to the normal to the surface of the sample lowers the spatial resolution of the image, thereby decreasing the precision of the determination of the crystal orientation.

To mitigate these drawbacks, document FR 2 988 841 proposes using a light beam. According to FR 2 988 841, this means a scanning electron microscope (see page 2, lines 13-25 of FR 2 988 841) and more generally an acquiring device employing a beam of charged particles is not needed.

According to FR 2 988 841, the use of a light beam makes it possible to obtain a method for mapping the crystal orientations of grains of a sample, which is compatible with industrial manufacturing constraints (see page 3, lines 21-23).

More precisely, FR 2 988 841 teaches the skilled person that the use of a light beam allows a mapping method that is simple, rapid and inexpensive to implement to be obtained. To be able to implement the method described in FR 2 988 841, the surface of the analyzed sample must be rough (see page 1, lines 3-9), in contrast to methods using a beam of charged particles, which require the surface of the analyzed sample to be polished.

In the context of the present invention, the expression "polished face" is understood to mean a surface that has been polished with a range of different grain sizes typically down to a grain size of 3 μm (diamond slurry for example) or that has more preferably undergone vibratory polishing in a colloidal silica slurry.

However, such a method has many drawbacks. In particular the spatial resolution of the images acquired using an acquiring device employing a light beam is not high enough to allow variations in crystal orientation inside a grain to be detected. Specifically, in FR 2 988 841, the lowest spatial resolution is equal to half the wavelength of the light beam. In other words, it is not possible with the method described in FR 2 988 841 to distinguish a difference in crystal orientation between two points separated by a distance smaller than half the wavelength.

Moreover, FR 2 988 841 does not allow intensities to be measured for two points of a given grain, but only an average intensity to be estimated for all the points of a given grain.

One aim of the present invention is to provide a method for mapping the crystal orientations of a sample made of polycrystalline material from images acquired using an acquiring device emitting a beam of charged particles (ions or electrons), and allowing at least one of the drawbacks mentioned above with reference to the EBSD technique to be mitigated. More precisely, one aim of the present invention is to provide a simple, rapid and inexpensive method for mapping the crystal orientations of a sample made of polycrystalline material, on the basis of images acquired using an acquiring device emitting a beam of charged particles.

SUMMARY OF THE INVENTION

For this purpose, the invention provides a method for mapping the crystal orientations of a sample having a polished surface, the method comprising:
- receiving a series of images of the sample, which images are acquired by an acquiring device, the images being acquired in different sample irradiation geometries, each image including pixels representing the intensities of points of the sample in a respective irradiation geometry;
- estimating at least one intensity profile for at least one point of the material from the series of images, each intensity profile representing the intensity associated with the point in question as a function of irradiation geometry for each image of the series; and
- determining a crystal orientation for each point in question of the material by comparing the intensity profile associated with said point in question to theoretical signatures of intensity profiles of known crystal orientations, which signatures are contained in a database.

In the context of the present invention, the expression "polished face" is understood to mean a surface that has been polished with a range of different grain sizes typically down to a grain size of 3 μm (diamond slurry for example) or that has more preferably undergone vibratory polishing in a colloidal silica slurry.

The following are preferred but nonlimiting aspects of the method according to the invention:
- the estimating step comprises, for each point in question of the material, grouping homologous pixels representing said point in question in the images of the series of images, and generating a plot of the intensity of the point in question as a function of irradiation geometry;
- the images of the series of images are acquired:
  - at a constant angle of inclination between the normal to the surface of the sample and the axis of the beam of charged particles; and
  - at different angles of rotation about the normal to the surface of the sample;
- the method furthermore comprises a step of correcting the constant angle of inclination and a step of rectifying images of the series of images, said converting step consisting in turning those images of the series of images which were obtained at a nonzero angle of rotation so as to make them correspond to an image obtained at a zero angle of inclination;
- the angle of rotation between two successive images of the series of images varies by a step comprised between 1° and 15°;
- increasing the size of the step allows acquisition time to be decreased since the number of images in the series of images is decreased;
- the dynamic range of the angles of rotation (β0-β4) is larger than or equal to 180°, preferably larger than or equal to 270° and even more preferably equal to 360°;
- the expression "dynamic range" is understood to mean the difference between the angle of rotation of an initial image and the angle of rotation of a final image of the series of images;
- the higher the dynamic range, the smaller the risk of error in the determination of a crystal orientation;
- specifically, for a dynamic range equal to 180°, the intensity profile of a point of the sample may correspond to a plurality of theoretical signatures;
- using a dynamic range higher than or equal to 270° and even more preferably equal to 360° allows ambiguity in the theoretical signatures associable with a given intensity profile to be removed;
- the images of the series of images are acquired at different angles of inclination between the surface of the sample and a plane perpendicular to the axis of the beam of charged particles (i.e. ions or electrons) emitted by the acquiring device;
- the angle of inclination of each image of the series of images is comprised between −60° and +60°;
- the angle of inclination between two successive images of the series of images varies by a step comprised between 1° and 10°;
- the method furthermore comprises a step of deforming images of the series of images, said deforming step consisting in stretching those images of the series of images which were obtained at a nonzero angle of inclination so as to make them correspond to an image obtained at a zero angle of inclination;
- the method furthermore comprises acquiring, in an acquiring device such as a focused ion beam device, a series of images of the polycrystalline material at different angles of inclination between the surface of the material and a plane perpendicular to the axis of the beam of charged particles, each image including pixels representing the intensity of points of the material at a respective angle of inclination;
- the method furthermore comprises the following steps:
  - calculating an intermediate segmented image for some and even more preferably all the images of the series of images, a first value being assigned to those pixels of the image of the series of images to obtain a segmented image; and
  - superposing the intermediate segmented images to form a final segmented image.

The invention also relates to a computer program product comprising programming code instructions intended to execute the steps of the method described above when said program is executed on a computer.

BRIEF DESCRIPTION OF THE FIGURES

Other features, aims and advantages of the present invention will become more clearly apparent from the following description, which is purely illustrative and nonlimiting and must be read with regard to the appended drawings, in which.

DETAILED DESCRIPTION

Figure 1:
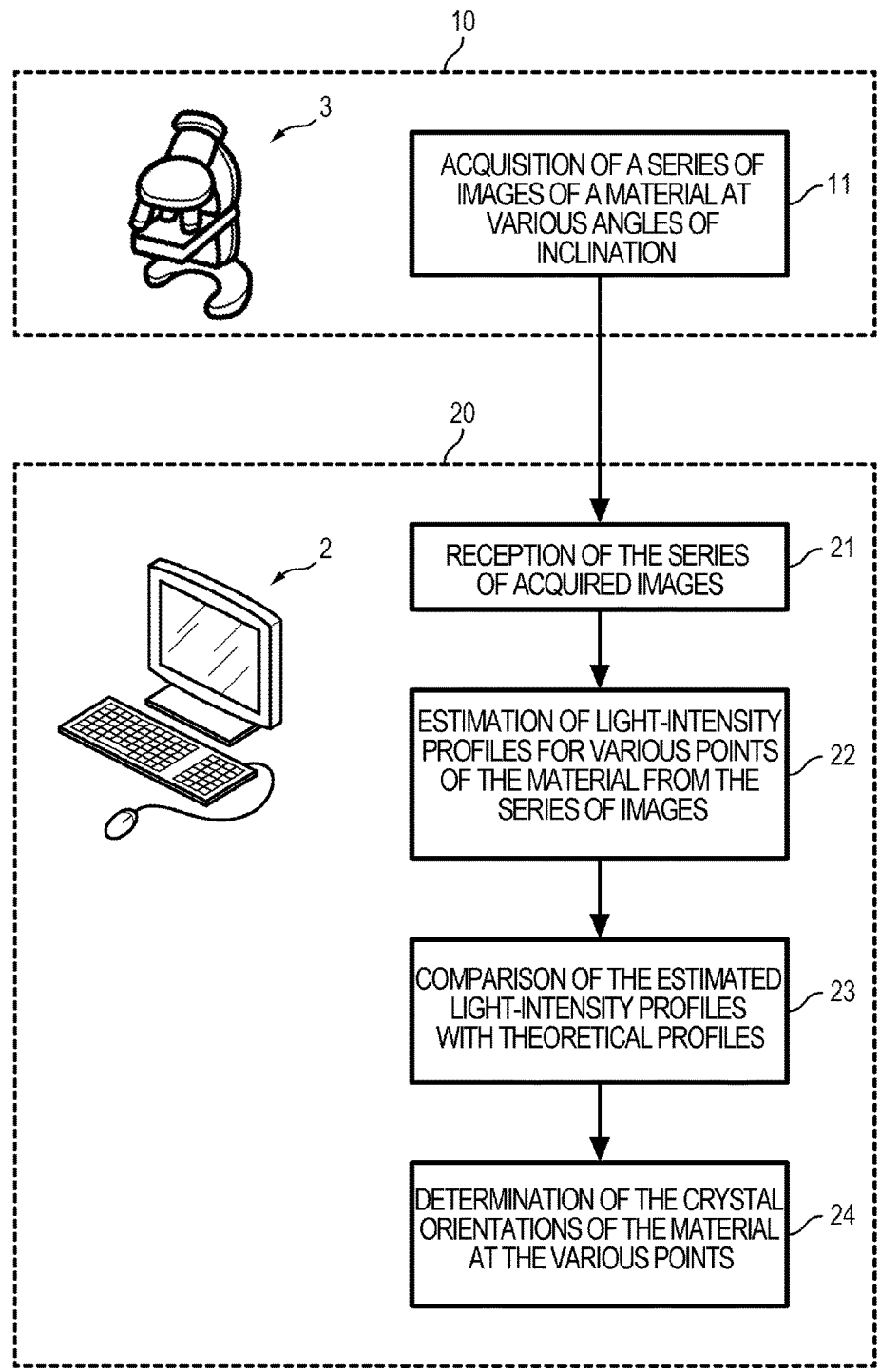
FIG. 1 illustrates an exemplary method for mapping the crystal orientation of a sample made of polycrystalline material.

A method for mapping the crystal orientations of a sample of polycrystalline material will now be described in more detail with reference to FIGS. 1 to 4.

This method may be implemented to determine the crystal orientation in each grain 41-46 of a sample made of polycrystalline material. The polycrystalline material may be a metal, a ceramic or any other polycrystalline material for which it is desired to map crystal orientations.

In a first phase 10 of the method, a plurality of images of the sample of polycrystalline material are acquired.

In a second phase 20 of the method, the acquired images are processed in order to determine the crystal orientations of the grains 41-46 of the sample made of polycrystalline material.

It is known that the intensity of an irradiated crystal under directional irradiation depends on the orientation of the crystal with respect to the direction of the beam used. In the case of a polycrystalline material, the intensity of each grain 41-46 therefore varies as a function of the orientation of the crystal with respect to the direction of the beam used.

The method described below is based on the use of this effect to determine the crystal orientations of the various constituent grains 41-46 of the sample made of polycrystalline material.

Acquiring Phase

The first phase comprises acquiring a series of images 4a-4e of the sample of polycrystalline material. The acquiring phase is implemented in an acquiring device suitable for emitting a beam of charged particles (ions or electrons) from a source and for collecting the particles emitted by the sample with a detector.

The acquiring device may be a scanning electron microscope 3 known to those skilled in the art and which will be briefly described below.

A scanning electron microscope functions by generating, from a source, a primary beam of scanning electrons that strike a sample, a surface of which is reproduced in image form.

As a result, secondary and backscattered electrons are emitted by the surface of the sample and their respective paths are opposite in direction to the original direction of the beam, which is perpendicular to the area of the sample (known as the axial direction), and at divergent angles to the latter direction.

The emitted electrons are collected by a detector, which is placed above the sample. The detector generates a signal from the collected electrons emitted from the surface of the sample when it is exposed to the electron beam.

The signal originating from the detector is typically processed to create an image of the surface of the sample.

As a variant, the acquiring device may be a focused ion beam device. The operating principle of a focused ion beam device (or FIB) is similar to that of scanning electron microscope (SEM).

Focused ion beam devices however differ from scanning electron microscopes in that they use a beam of focused ions, generally gallium ions, to irradiate the sample.

The use of a focused ion beam device allows the variation in intensity between the various grains 41-46 of the sample of polycrystalline material to be increased.

Whatever the acquiring device used, the latter allows a series of images 4a-4e of the sample to be acquired.

Advantageously, the images 4a-4e of the sample are acquired in various irradiation geometries. More precisely, and considering a given grain of the polycrystalline sample, each image is acquired with a different orientation of the beam with respect to the crystal structure of the grain.

For a given grain, since the intensity received by the detector depends on its crystal orientation with respect to the beam, the intensity of this grain is different in the various images of the series of images.

Two different acquiring modes allow series of images that may be used to determine the crystal orientations of the grains in the observed zone to be obtained.

Figure 2:
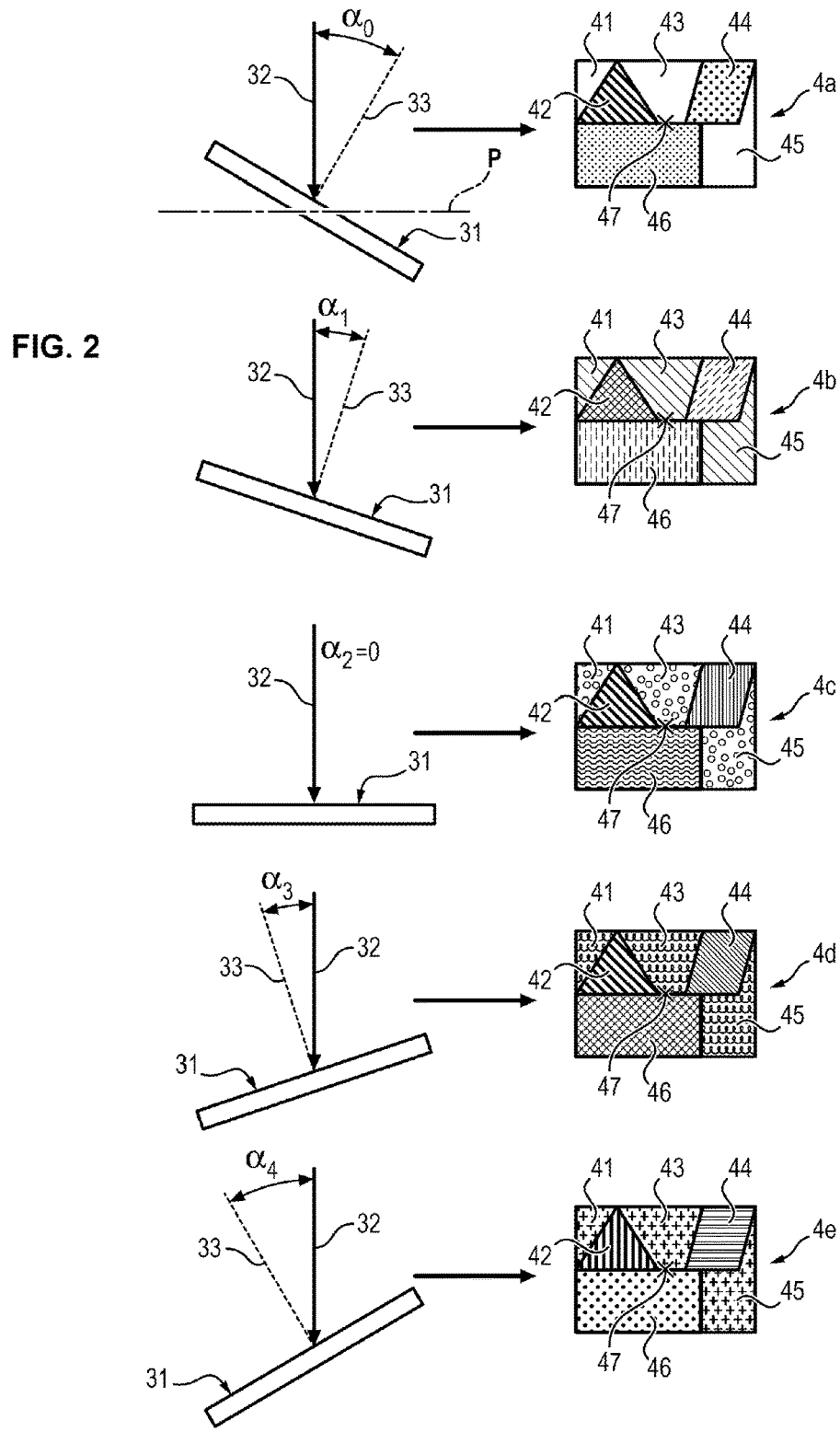
FIG. 2 illustrates a first mode for acquiring images of the sample made of polycrystalline material at various angles of inclination.

Acquiring Mode No. 1—FIG. 2

FIG. 2 illustrates a first acquiring mode in which the images of the series of images are acquired as an angle of inclination is varied.

In the context of the present invention, the expression "angle of inclination" is understood to mean the angle "α" between the surface 31 of the material and a plane P perpendicular to the axis 32 of the beam of charged particles. Thus, the angle α corresponds to the angle between the normal 33 to the surface 31 of the material and the axis 32 of the beam of charged particles.

To vary the irradiation geometry between the beam of charged particles and the various constituent grains of the zone to be analyzed, the sample may be rotated about a pivot axis that is perpendicular to the axis 32 of the beam of charged particles, and therefore contained in the plane P. In this way, the angle of inclination is varied as the successive images are acquired.

Advantageously, the angle of inclination a may vary in a range comprised between −60° and +60°. This allows an angular range to be obtained that is large enough for the crystal orientation of the various grains 41-46 of the material to be determined in the second phase 20.

Depending on the targeted application and the needs of the user, the angle of inclination may be modified in steps of between the smallest step allowable by the control system of the goniometric stage used (for example 0.001°, or typically 1° in a SEM) and typically several degrees, between two successive acquisitions.

The operating principle of the acquiring device is as follows. The sample is attached to a holder that is rotatable about the pivot axis, which is perpendicular to the axis 32 of the beam of charged particles. The holder is rotated to a first extreme position (for example α0=−60°). A first image is acquired. The holder is then rotated by an angle corresponding to a chosen angular step, thereby causing the rotation of the sample. A second image of the sample is acquired. The rotating and acquiring steps are then reiterated until a second extreme position is reached (for example α4=+60°).

In this way:
  a series of 120 images is obtained at an angle of inclination varying between −60° and 60° in the case of a step size of 1°; or
  a series of 60 images is obtained at an angle of inclination varying between −60° and 60° in the case of a step size of 2° or an angle of inclination varying between −30° and 30° in the case of a step size of 1°.

The series of images is then transmitted to a processing device for implementation of the second phase of the method.

Figure 3:
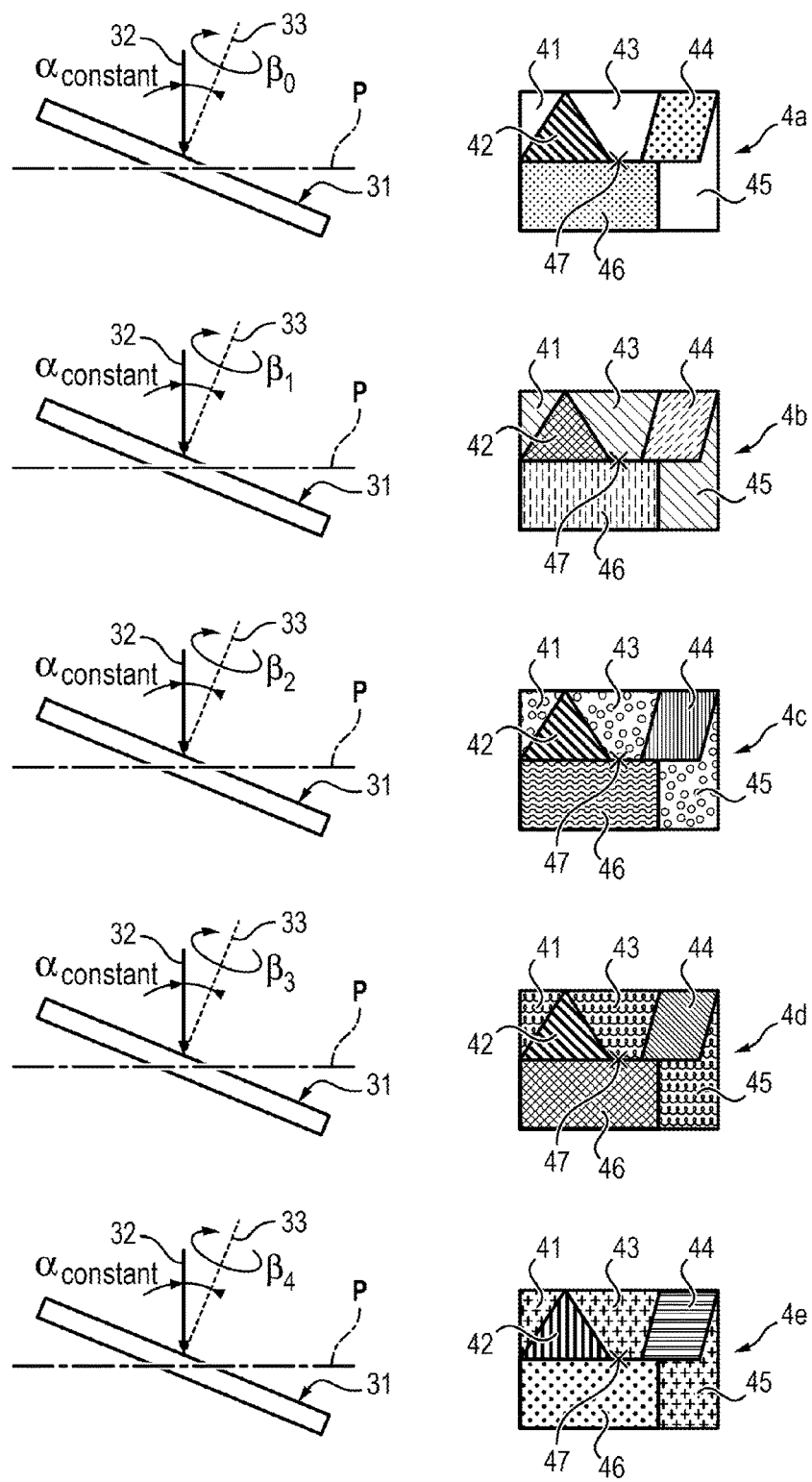
FIG. 3 illustrates a second mode for acquiring images of the sample made of polycrystalline material at various angles of rotation.

Acquiring Mode No. 2—FIG. 3

FIG. 3 illustrates a second acquiring mode in which the images of the series of images are acquired by varying an angle of rotation.

In the context of the present invention and for this second acquiring mode, the expression "angle of rotation" is understood to mean the angle "β" of rotation about the normal 33 to the surface 31 of the material. The angle of inclination $\alpha_{constant}$, defined as being the angle between the surface and the beam of charged particles, is advantageously set to about 40° to optimize the acquisition of the images.

Of course, those skilled in the art will understand that another nonzero angle of inclination may be used, for example a value comprised between [−80, 0 [and]0, +80°]. To vary the irradiation geometry between the beam of charged particles and the various constituent grains of the zone to be analyzed, the sample may be rotated about the normal 33 to the surface 31 of the material as successive images are acquired. In this way, the angle of rotation β is varied as the successive images are acquired.

Advantageously, the angle of rotation may cover 360°, i.e. a complete revolution. Depending on the targeted application and the needs of the user, the angle of rotation may be modified in steps of between the smallest step allowable by the control system of the goniometric stage used (for example 0.001°, or typically 1° in an SEM) and typically several degrees, between two successive acquisitions.

The operating principle of the acquiring device is as follows. The sample is attached to a holder that is rotatable about the pivot axis, which is perpendicular to the normal 33 to the surface 31 of the material. The holder is rotated to an initial position (for example $\beta_0$=0°. A first image is acquired. The holder is then rotated by an angle corresponding to the chosen angular step, thereby causing the rotation of the sample. A second image of the sample is acquired. The rotating and acquiring steps are then reiterated until a final position is reached (for example $\beta_n$=360°.

For example, for a complete revolution (i.e. angle of rotation varying from 0 to 360°) a series of 180 images is obtained for a step size of 2°, or a series of 360 images is obtained for a step size of 1°.

The series of images is then transmitted to a processing device for implementation of the second phase of the method.

In addition, since the angle of emission of the electrons from the surface of the sample toward the detector is invariant during the acquisition of the series of images, the average intensity of an image is equal in the various images of the series.

This means there is no need for a step of harmonizing the average intensity in the various images though such a step will possibly be implemented in the case of an acquisition according to the first acquiring mode.

Specifically, in the first acquiring mode, the variation in the angle of inclination means that there is a variation in the angle of emission of the electrons from the surface of the sample toward the detector (and therefore in the average intensity in the various images of the series).

Processing Phase

The processing device 2 allows the crystal orientation of the sample of material to be mapped.

The processing device 2 may comprise a processor especially allowing intensity profiles to be estimated as will be described in more detail below.

The processor is for example one or more computers, one or more processing units, one or more microcontrollers, one or more microcomputers, one or more programmable controllers, one or more application-specific integrated circuits, one or more other programmable circuits or one or more other devices (such as a workstation) that include a computer.

The processing device 2 may be integrated into the acquiring device 3, or be separate from the acquiring device 3.

The processor is coupled to a memory (or to more than one memories), which may be integrated into or separate from the processor. The memory may be a ROM/RAM memory, a USB key or a memory of a central server. This memory may allow programming code instructions intended to execute the steps of the processing phase 20, or other data used by the processor, to be stored.

In a first step, the processing device 2 receives the images 4a-4e of the series of images acquired by the acquiring device 3. Each acquired image 4a-4e is composed of pixels the gray levels of which—comprised between 0 and 255 or more if the acquired images are coded with a higher number of bits (for example 16 or 32 bits)—are representative of the electronic intensities received by the detector.

More precisely, the gray level of each pixel is representative of the intensity of a corresponding point of the sample. This intensity depends on the crystal orientation at the point in question and the angle defined by the acquisition geometry (i.e. positions of the source and detector with respect to the sample).

The images 4a-4e of the series of images comprise homologous pixels corresponding to a given point 47 of the sample of polycrystalline material.

The gray level of the homologous pixels varies between two successively acquired images since the acquisition geometry (i.e. angle of inclination a) varies as these successive images are acquired.

Thus, the intensity of a given point 47 of the sample—and therefore more generally of a given grain 41-46—varies in the images of the series of images 4a-4e, as illustrated in FIG. 2.

For the acquiring mode 1, since the images are obtained at various angles of inclination, the latter are deformed with respect to one another. For this reason the method may comprise a step of deforming images of the series of images, said deforming step consisting in stretching those images of the series of images which were obtained at a nonzero angle of inclination so as to make them correspond to an image obtained at a zero angle of inclination.

For the acquiring mode 2, it is also necessary to correct for the inclination of the sample, as was the case for the images obtained with the acquiring mode 1. However, this angle of inclination is the same for all the images. However, since the images were obtained at various angles of rotation of the sample, the method may then comprise a step of rectifying images of the series of images, said rectifying step consisting in pivoting those images of the series of images which were obtained at a nonzero angle of rotation so as to make them correspond to an image obtained at a zero angle of rotation.

In another step 22 of the method, intensity profiles are estimated.

For each point of the sample, homologous pixels of the various images are grouped. The value of each homologous pixel—which represents an intensity—is plotted as a function of the angle used to acquire the image to which the homologous point belongs.

Figure 4:
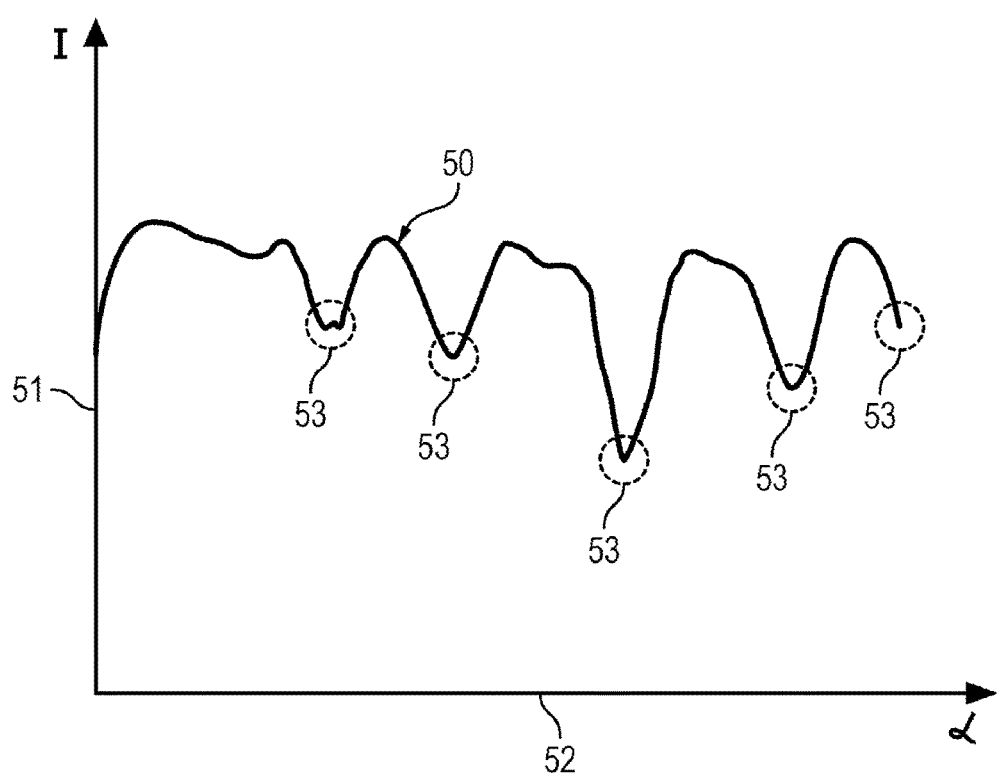
FIG. 4 illustrates an exemplary intensity profile representing the intensity of a point of the polycrystalline material as a function of the angle used for the acquisition.

An exemplary intensity profile 50 estimated for a point of a sample is illustrated in FIG. 4. This intensity profile 50 shows the intensity 51 of the point of the sample as a function of angle 52. It may be seen that the intensity 51 varies as a function of angle 52. In particular, the intensity profile comprises four troughs 53 corresponding to drops in intensity. Apart from these four troughs 53, the intensity of the point of the sample remains substantially constant whatever the angle.

Instead of estimating an intensity profile for each point of the sample, the estimating step may be implemented at one, two, or three points in each grain 41-46 of the sample. This allows the processing phase to be accelerated. In this case, the method comprises a step of selecting the points of the sample on which the estimating step is to be carried out. This selecting step may be automatic or manual (i.e. carried out by the user).

To facilitate the implementation of the selecting step, the method may comprise a step of detecting the boundaries of the grains, this step being based on any boundary detecting algorithm known to those skilled in the art.

The boundaries are advantageously detected in a plurality of images of the series of images and preferably in all the images of the series of images. Specifically, implementing the boundary detecting step with a single image of the series of images may not allow the boundaries of all the grains to be identified since, in certain cases, two adjacent grains may have the same gray level in a given image of the series of images. For this reason, it is preferable to carry out the boundary detecting step with a plurality of images. At the end of the boundary detecting step, a plurality of intermediate segmented images are obtained.

These intermediate segmented images are then superposed to form the final segmented image of the grains of the sample.

One or more points are then selected in each grain of the grain-segmented image of the sample and intensity profiles estimated for each selected point.

An intensity profile may be interpreted as follows. When the intensity is constant, then the orientation between the beam and the crystal plane at the point in question is indeterminate. When the intensity varies, then the beam is almost parallel to the crystal plane at the point in question of the sample.

The amplitude of the drop in intensity depends on the type of crystal plane. For example for the cubic structure of titanium nitride (TiN), when the beam becomes parallel to a [1 1 1] plane, the drop in intensity is smaller than when the beam becomes parallel to a [1 1 0] plane. Likewise, when the beam becomes parallel to a [1 1 0] plane, the drop in intensity is smaller than when the beam becomes parallel to a [1 0 0] plane. Thus, the amplitude of the drop in intensity allows the type of crystal plane present at a point of the sample to be defined.

However, this interpretation does not allow the crystal orientation of the points of the sample to be determined by a method of direct calculation. Specifically, if during the acquisition a plurality of [1 1 1] crystal planes are for example parallel to the beam at a given angle of inclination, two low-amplitude troughs may cause a large-amplitude trough to appear by addition of the two effects, thereby leading to an error in the characterization of the crystal plane at a point of the sample.

For this reason, the inventors propose to compare (step 23) each intensity profile to theoretical intensity-profile signatures for which the crystal orientation is known. These theoretical signatures are contained in a database for the seven crystal systems, namely:
the triclinic crystal system,
the monoclinic crystal system,
the orthorhombic crystal system,
the tetragonal crystal system,
the trigonal crystal system,
the hexagonal crystal system, and
the cubic crystal system.

Each estimated intensity profile is therefore compared (step 23) to theoretical intensity-profile signatures contained in the database. The crystal orientation is determined to be the orientation of the theoretical signature that has the highest correlation with the estimated intensity profile.

The estimating and comparing steps are repeated for the various points of the sample. Thus a map of the crystal orientations of the grains of the sample of polycrystalline material is obtained.

The reader will understand that many modifications may be made to the method described above without actually departing from the scope of the disclosed novel teachings.

For example, the method may be used to determine the crystal orientation of a single-crystal material.

Hence, it will be understood that the examples given above are merely illustrations and that they are in no case meant to be limiting.

The invention claimed is:

1. A method for mapping the crystal orientations of a sample having a polished surface, the method comprising:
receiving a series of images of the sample, which images are acquired by an acquiring device suitable for emitting a beam of charged particles onto the polished surface, the images being acquired in different sample irradiation geometries, each image including pixels representing the intensities of points of the sample in a respective irradiation geometry;
estimating at least one intensity profile for at least one point of the material from the series of images, each intensity profile representing the intensity associated with the point in question as a function of irradiation geometry; and
determining a crystal orientation for each point in question of the material by comparing the intensity profile associated with said point in question to theoretical signatures of intensity profiles of known crystal orientations, which signatures are contained in a database.

2. The method as claimed in claim 1, wherein the estimating step comprises, for each point in question of the material, grouping homologous pixels representing said point in question in the images of the series of images, and generating a plot of the intensity of the point in question as a function of irradiation geometry.

3. The method as claimed in claim 1, wherein the images of the series of images are acquired:
at a constant angle of inclination between the normal to the surface of the sample and the axis of the beam of charged particles; and
at different angles of rotation about the normal to the surface of the sample.

4. The method as claimed in claim 3, which furthermore comprises a step of rectifying images of the series of images, said converting step consisting in turning those images of the series of images which were obtained at a nonzero angle of rotation so as to make them correspond to an image obtained at a zero angle of inclination.

5. The method as claimed in claim 3, wherein the angle of rotation between two successive images of the series of images varies by a step comprised between 1° and 15°.

6. The method as claimed in claim 3, wherein the dynamic range of the angles of rotation is larger than or equal to 180°, preferably larger than or equal to 270° and even more preferably equal to 360°.

7. The method as claimed in claim 1, wherein the images of the series of images are acquired at different angles of inclination between the surface of the sample and a plane perpendicular to the axis of the beam of charged particles emitted by the acquiring device.

8. The method as claimed in claim 7, wherein the angle of inclination of each image of the series of images is comprised between −60° and +60°.

9. The method as claimed in claim 7, wherein the angle of inclination between two successive images of the series of images varies by a step comprised between 1° and 10°.

10. The method as claimed in claim 7, which furthermore comprises a step of deforming images of the series of images, said deforming step consisting in stretching those images of the series of images which were obtained at a nonzero angle of inclination so as to make them correspond to an image obtained at a zero angle of inclination.

11. The method as claimed in claim 1, which furthermore comprises acquiring, in an acquiring device such as a focused ion beam device, a series of images of the polycrystalline material at different angles of inclination between the surface of the material and a plane perpendicular to the axis of the beam of charged particles, each image including pixels representing the intensity of points of the material at a respective angle of inclination.

12. The method as claimed in claim 1, which furthermore comprises the following steps:
    calculating an intermediate segmented image for each image of the series of images; and
    superposing the intermediate segmented images to form a final segmented image.

13. A non-transitory computer program product comprising programming code instructions intended to execute the steps of a method for mapping the crystal orientations of a sample having a polished surface when said program is executed on a computer, the method comprising:
    receiving a series of images of the sample, which images are acquired by an acquiring device suitable for emitting a beam of charged particles onto the polished surface, the images being acquired in different sample irradiation geometries, each image including pixels representing the intensities of points of the sample in a respective irradiation geometry;
    estimating at least one intensity profile for at least one point of the material from the series of images, each intensity profile representing the intensity associated with the point in question as a function of irradiation geometry; and
    determining a crystal orientation for each point in question of the material by comparing the intensity profile associated with said point in question to theoretical signatures of intensity profiles of known crystal orientations, which signatures are contained in a database.

14. The non-transitory computer program product according to claim 13, wherein the estimating step comprises, for each point in question of the material, grouping homologous pixels representing said point in question in the images of the series of images, and generating a plot of the intensity of the point in question as a function of irradiation geometry.

15. The non-transitory computer program product according to claim 13, wherein the images of the series of images are acquired:
    at a constant angle of inclination between the normal to the surface of the sample and the axis of the beam of charged particles; and
    at different angles of rotation about the normal to the surface of the sample.

16. The non-transitory computer program product according to claim 15, wherein the method further comprises a step of rectifying images of the series of images, said converting step consisting in turning those images of the series of images which were obtained at a nonzero angle of rotation so as to make them correspond to an image obtained at a zero angle of inclination.

17. The non-transitory computer program product according to claim 15, wherein the angle of rotation between two successive images of the series of images varies by a step comprised between 1° and 15°.

18. The non-transitory computer program product according to claim 15, wherein the dynamic range of the angles of rotation is larger than or equal to 180°, preferably larger than or equal to 270° and even more preferably equal to 360°.

19. The non-transitory computer program product according to claim 13, wherein the images of the series of images are acquired at different angles of inclination between the surface of the sample and a plane perpendicular to the axis of the beam of charged particles emitted by the acquiring device.

20. The non-transitory computer program product according to claim 19, wherein the angle of inclination of each image of the series of images is comprised between −60° and +60°.

21. The non-transitory computer program product according to claim 19, wherein the angle of inclination between two successive images of the series of images varies by a step comprised between 1° and 10°.

22. The non-transitory computer program product according to claim 19, wherein the method further comprises a step of deforming images of the series of images, said deforming step consisting in stretching those images of the series of images which were obtained at a nonzero angle of inclination so as to make them correspond to an image obtained at a zero angle of inclination.

23. The non-transitory computer program product according to claim 13, wherein the method further comprises acquiring, in an acquiring device such as a focused ion beam device, a series of images of the polycrystalline material at different angles of inclination between the surface of the material and a plane perpendicular to the axis of the beam of charged particles, each image including pixels representing the intensity of points of the material at a respective angle of inclination.

* * * * *